(12) United States Patent
Sakaguchi et al.

(10) Patent No.: US 8,012,138 B2
(45) Date of Patent: Sep. 6, 2011

(54) NURSING PAD

(75) Inventors: Satoru Sakaguchi, Kagawa-ken (JP); Ayami Suga, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 225 days.

(21) Appl. No.: 11/531,358

(22) Filed: Sep. 13, 2006

(65) Prior Publication Data

US 2007/0100310 A1 May 3, 2007

(30) Foreign Application Priority Data

Nov. 1, 2005 (JP) ................................ 2005-318429

(51) Int. Cl.
*A61F 13/15* (2006.01)

(52) U.S. Cl. ................ 604/385.07; 604/385.201; 2/104; 450/37

(58) Field of Classification Search ............. 604/385.07, 604/385.201; 2/53–58, 104; 450/36–37
See application file for complete search history.

(56) References Cited

U.S. PATENT DOCUMENTS

| | | | | |
|---|---|---|---|---|
| 2,891,544 A | * | 6/1959 | London | 604/379 |
| 3,442,268 A | * | 5/1969 | Bird | 604/380 |
| 3,891,544 A | | 6/1975 | Becker et al. | |
| 4,074,721 A | | 2/1978 | Smits et al. | |
| 4,674,510 A | | 6/1987 | Sneider | |
| 5,104,396 A | * | 4/1992 | Oatley et al. | 604/379 |
| 5,683,286 A | * | 11/1997 | Kielland | 450/37 |
| 5,690,536 A | | 11/1997 | Madden et al. | |
| 6,264,529 B1 | | 7/2001 | Logue | |
| 6,878,034 B1 | * | 4/2005 | Cisneros | 450/57 |
| 6,945,966 B2 | * | 9/2005 | Mikami | 604/346 |
| 2002/0022815 A1 | | 2/2002 | Yamaji | |
| 2004/0154068 A1 | | 8/2004 | Gorringe et al. | |

FOREIGN PATENT DOCUMENTS

| | | |
|---|---|---|
| JP | S59-150438 U | 10/1984 |
| JP | 75619 | 1/1995 |
| JP | 721711 | 4/1995 |
| JP | 721712 | 4/1995 |
| JP | 721713 | 4/1995 |
| JP | 07-300702 A | 11/1995 |
| JP | 08060409 | 3/1996 |
| JP | 08196603 | 8/1996 |
| JP | 2000178805 | 6/2000 |
| JP | 2004-332178 A | 11/2004 |

OTHER PUBLICATIONS

International Search Report for PCT/JP2006/317880 issued Nov. 7, 2006.
Office Action issued to U.S. Appl. No. 11/534,742, mailed Jun. 4, 2008.
Supplemental European Search Report issued to EP Application No. 06783240.2, mailed Aug. 26, 2010.

* cited by examiner

*Primary Examiner* — Lynne Anderson (74) *Attorney, Agent, or Firm* — Lowe, Hauptman, Ham & Berner, LLP (57) ABSTRACT

A nursing pad has a first folding portion, which serves as a folding axis that allows the nursing pad to be folded thereal-ong, provided such that it passes near an apex of the nursing pad, and extends up to the perimeter thereof. Furthermore, the nursing pad includes a fastening element, which allows the nursing pad to be fastened to the wearer's clothing, provided to a portion other than the first folding portion and the linear portion orthogonal to the first folding portion.

18 Claims, 5 Drawing Sheets

NURSING PAD

This application is based on and claims the benefit of priority from Japanese Patent Application No. 2005-318429, filed on 1 Nov. 2005, the content of which is incorporated herein by reference.

BACKGROUND OF THE INVENTION

1. Field of the Invention

The present invention relates to a disposable nursing pad which can be worn again after breast-feeding, and which does not lose shape during breast-feeding.

2. Related Art

In general, a great amount of a mother's milk is secreted in response to the sucking stimulation from a baby. However, in some cases, the mother's milk leaks without such a sucking stimulation. Also, the left and right breasts both respond together. Accordingly, when a mother's breast feeds a baby, the mother's milk is also secreted from the other breast. In order to keep a wearer's clothing dry from such undesired leakage of the mother's milk, a nursing mother wears nursing pads in contact with the inner face of the wearer's underclothing such as a bra or the like, which envelope the breasts, thereby absorbing excess milk.

In general, a nursing mother, wearing a nursing pad on the inner face of a bra, displaces the bra downward and obliquely to expose her breast. In this stage, the nursing pad is sandwiched between the bra and the outer face of the lower portion of the breast, leading to the application of pressure on the nursing pad. This often leads to the nursing pad losing its shape. A nursing pad which has lost its shape is adhered to the inner face of the bras without recovery of shape due to the action of an adhesive applied to the clothing for preventing displacement of the nursing pad. This leads to difficulty for the wearer when wearing the nursing pad again in a restored state.

Figure 10:
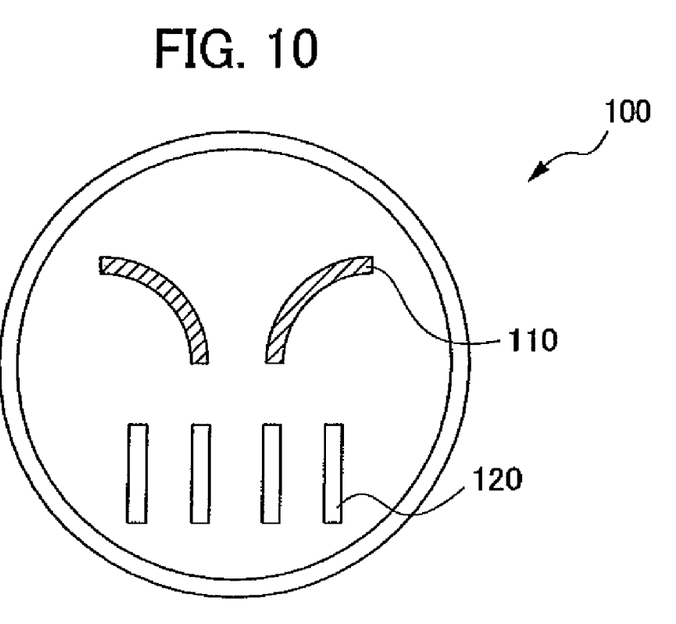
FIG. 10 is a plan view of a conventional nursing pad main body as viewed from the outside (from the side of the clothing).

On the other hand, Japanese Unexamined Patent Application Publication No. 2000-178805 (herein after Patent document 1) discloses a nursing pad having a structure in which recessed grooves 110 are formed across the portion which is to be in contact with the wearer's nipple (see FIG. 10). With such a nursing pad disclosed in Patent document 1, the nursing pad is manufactured without heat application. This provides a dome-shaped nursing pad corresponding to the shape of the wearer's breast while keeping the nursing pad feeling soft.

As described above, the nursing pad disclosed in Patent document 1 has a structure in which the recessed grooves 110 are formed on both sides across the portion which is to be in contact with the wearer's nipple. However, the portions where the recessed grooves 110 are formed differ from the portions along which the nursing pad often twists at the time of breast-feeding. Accordingly, the nursing pad easily twists excessively with each of the recessed grooves 110 as a folding axis, leading to the nursing pad losing its shape. This leads to difficulty in the wearer wearing the nursing pad again.

The present invention has been made in view of the aforementioned problems. Accordingly, it is an object thereof to provide a disposable nursing pad which can be worn again after breast-feeding, and which does not lose its shape during breast-feeding.

SUMMARY OF THE INVENTION

The present inventors have diligently researched the fact that, while a nursing mother is breast-feeding, when the nursing mother displaces the bra downward and obliquely, in order to expose/unexposed a breast, the nursing pad often twists obliquely. As a result, the present inventors have made an arrangement in which a nursing pad main body has a first folding portion, which serves as a folding axis that allows the nursing pad main body to be folded therealong, provided such that it passes through near an apex of the aforementioned nursing pad, and extends up to around the perimeter thereof, with a fastening device, which allows the nursing pad main body to be fastened to the wearer's clothing, being provided to a portion other than the first folding portion, and the linear portion orthogonal to the first folding portion. Furthermore, the present inventors have found that such an arrangement is capable of solving the aforementioned problems, whereby the present inventors have achieved the present invention. More specifically, the present invention provides the following arrangements.

A first aspect of the present invention is a nursing pad including a pair of nursing pad main bodies formed in a shape that allows the wearer's breast to be enveloped, in which the nursing pad main body includes: a liquid-impermeable sheet that forms the external shape of the nursing pad main body; a liquid-permeable sheet which is provided on the inner face of the liquid-impermeable sheet with a perimeter thereof being adhered to the perimeter of the liquid-impermeable sheet; an absorber which is provided between the liquid-impermeable sheet and the liquid-permeable sheet, and which has a function of absorbing and holding the mother's milk; a first folding portion, which serves as a folding axis that allows the nursing pad main body to be folded therealong; and a fastening means, which allows the nursing pad main body to be fastened to the wearer's clothing, in which the first portion is formed such that it passes through near an apex of the nursing pad, and extends up to around the perimeter of the nursing pad, and in which the fastening means is provided to a portion of the liquid-impermeable sheet other than the first folding portion and the linear portion orthogonal to the first folding portion.

The nursing pad according to the first aspect of the present invention has the first folding portion that serves as a folding axis which allows the nursing pad main body to be folded therealong. The first folding portion is formed such that it passes through near the apex of the aforementioned nursing pad, and extends up to around the perimeter thereof. Furthermore, the fastening means, which allows the nursing pad main body to be fastened to the wearer's clothing, is provided to a portion of the liquid-impermeable sheet other than the first folding portion and the linear portion orthogonal to the first folding portion.

The wearer generally wears a nursing pad with the fastening means being positioned on the upper side. The reason is that such an arrangement allows the wearer to easily wear the nursing pad, and allows the wearer to expose the wearer's breast when the wearer breast-feeds a baby. Accordingly, the nursing pad main body described in the first aspect of the present invention has the first folding portion formed such that is passes through the wearer's body obliquely when it is being worn. The phrase "pass through the wearer's body obliquely" as used here means that it passes through the wearer's body obliquely with respect to the central axis, passing through the wearer's body in the vertical (longitudinal) direction when the wearer is in the standing position.

Figure 4:
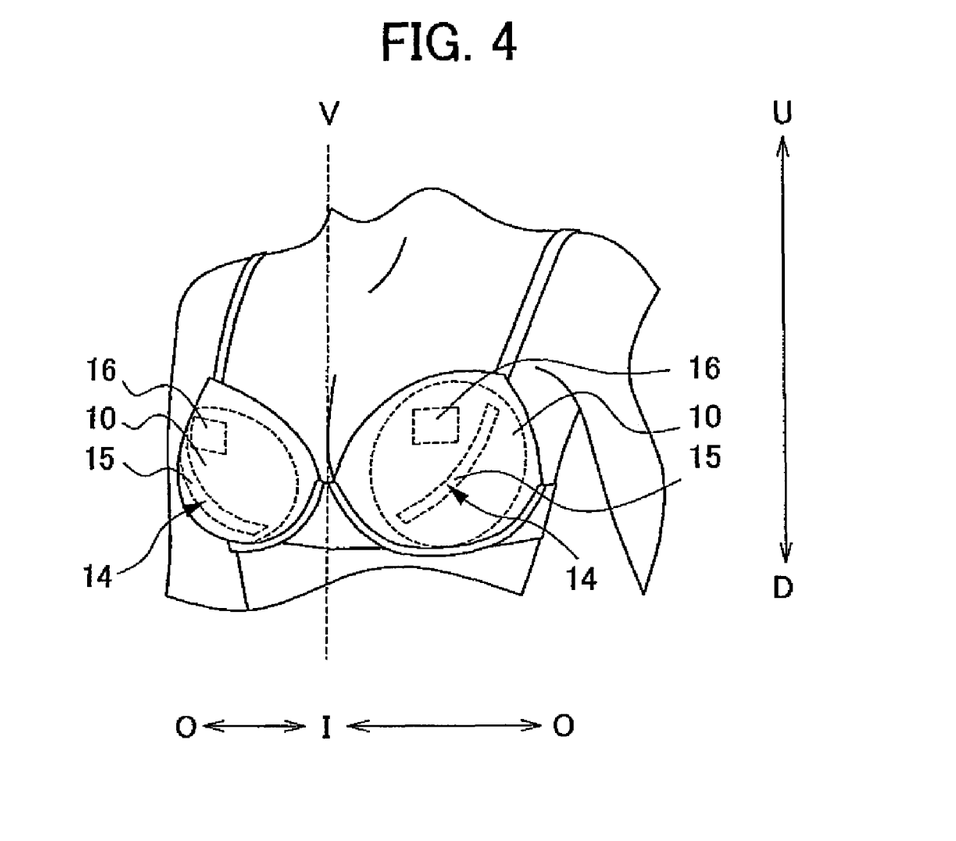
FIG. 4 is a diagram which shows the wearer wearing the nursing pad main body according to the first embodiment.

The term "upper portion" or "upper side" in this specification represents the side of the wearer's head along the vertical direction. On the other hand, "lower portion" or "lower side" as used here represents the side of the wearer's foot along the vertical direction. The term "outer side" as used here represents the side of the wearer's arm with respect to the wearer's body. On the other hand, the term "inner side" as used here represents the side of the central axis that passes through the center of the wearer's body having breasts. As shown in FIG. 4, the "center axis" is indicated by the line V, and the "upper portion" and "upper side" are indicated by reference symbol "U". Also, the "lower portion" and "lower side" are indicated by reference symbol "D". Also, the "outer side" is indicated by reference symbol "O", and the "inner side" is indicated by reference symbol "I".

The term "apex" in this specification represents the end of the curved surface which the nursing pad with a dome like shape or a conical shape has. When the perimeter of the nursing pad is in contact with a face, the apex is at the furthest most point from this face. The term "perimeter" means the vicinity of the circumferential edge.

The wearer knows the shape of a bra used in daily life. Accordingly, it is natural for the wearer to wear the nursing pad with the first folding portion being positioned such that it extends obliquely from the upper-outer side of the wearer's breast to the lower-inner side thereof. Accordingly, the nursing pad of the first aspect of the present invention has the first folding portion provided such that it extends obliquely from the upper-outer side of the wearer's breast to the lower-inner side thereof when it is being worn. With such an arrangement, in which the nursing pad is being worn with the first folding portion being positioned such that it extends obliquely from the upper-outer side of the wearer's breast to the lower-inner side thereof, the wearer displaces the bra downward and obliquely when the wearer breast-feeds a baby. In this case, the nursing pad main body is folded in a form following the shape of the wearer's breast with the first folding portion as a folding axis. That is to say, the nursing pad main body is folded along the first folding portion, thereby effectively preventing the nursing pad main body from losing its shape. This allows the wearer to easily wear the nursing pad again together with the bra in the normal state as before. Furthermore, such an arrangement prevents the mother's milk stored in the absorber from escaping due to the absorber being twisted.

Furthermore, the nursing pad of the first aspect of the present invention includes the fastening means provided to the side having the liquid-impermeable sheet. Such an arrangement allows the nursing pad to move on with the bra through the fastening means when the wearer wears the bra after breast-feeding. This effectively prevents the nursing pad main body from losing its shape, thereby allowing the wearer to easily wear the nursing pad in the normal state as before.

In a second aspect of the nursing pad as described in the first aspect of the present invention, further including a display region provided to a portion which allows the wearer to see the display region from the external side of the nursing pad main body, in which the display region gives the wearer instructions that the nursing pad main body should be worn with the first folding portion being positioned obliquely from the upper-outer side to the lower-inner side of the wearer's breast.

The nursing pad main body described in the second aspect of the present invention includes the display region which gives the wearer instructions that the nursing pad main body should be worn with the first folding portion being positioned obliquely from the upper-outer side to the lower-inner side of the wearer's breast. That is to say, with the nursing pad described in the first aspect of the present invention, the wearer wears it according to habitual practices. On the other hand, the nursing pad described in the second aspect of the present invention has a display region which gives the wearer instructions for the proper wearing method. Thus, the nursing pad described in the second aspect of the present invention allows the wearer to easily and properly wear the nursing pad, thereby providing the same advantages as described in the second aspect of the present invention in a surer manner.

In a third aspect of the nursing pad as described in the first or the second aspect of the present invention, the first folding portion is provided in a discontinuous manner.

The nursing pad described in the third aspect of the present invention has the first folding portion, which serves as a folding axis that allows the nursing pad to be folded thereaolong, formed in a discontinuous manner. Accordingly, such an arrangement provides the same advantages as those of the nursing pads described in first and second aspect of the present invention. Furthermore, with such an arrangement, the first folding portion is provided in a discontinuous manner. Accordingly, the absorber is not divided by the first folding portion 25. With such an arrangement, the mother's milk is absorbed by the entire area of the absorber. Accordingly, the water absorption capacity of the nursing pad main body is not divided, thereby providing superior water absorption capacity.

In a fourth aspect of the nursing pad as described in the third aspect of the present invention, the first folding portion is provided to a portion other than the portion with which the wearer's nipple is to be in contact with.

The nursing pad described in the fourth aspect of the present invention has the first folding portion, which serves as a folding axis that allows the nursing pad to be folded thereaolong, formed in a discontinuous manner, except for the portion with which the wearer's nipple is to be in contact with. In case in which the first folding portion, which serves as a folding axis that allows the nursing pad to be folded thereaolong, is provided to the portion with which the wearer's sensitive nipple is to be in contact with, such an arrangement leads to the wearer's discomfort. On the other hand, with the nursing pad described in the fourth aspect of the present invention, the first folding portion is not provided to the portion with which the wearer's nipple is to be in contact with. With such an arrangement, the wearer's nipple is not in contact with the first folding portion, thereby preventing the wearer's discomfort.

In a fifth aspect of the nursing pad as described in the first through fourth aspect of the present invention, the first folding portion has a stiffness of the absorber which is different from the stiffness of absorber around the first folding portion.

With the nursing pad described in fifth aspect of the present invention, there is a difference in the stiffness of the aforementioned absorber between the first folding portion and the portion there around. With such an arrangement, the nursing pad main body can be folded along the boundary across which the stiffness changes, thereby preventing the nursing pad main body from losing shape. The term "stiffness" as used in the present specification represents the degree to which an object resists losing shape due to application of external force on this object. Specifically, the absorber may be formed with less stiffness at the first folding portion than the portion around the first folding portion. Conversely, the absorber may be formed with higher stiffness at the first folding portion than the portion around the first folding portion. In either arrangement, the nursing pad main body is folded along the boundary, in cases in which the wearer displaces the bra downward and obliquely when the wearer breast-feeds a baby. Such an arrangement allows the wearer to easily wear it again, while effectively preventing the nursing pad main body from losing its shape. Note that the term "stiffness" as used in the present specification represents the stiffness measured by a Gurley bending resistance tester. The term "Gurley bending resistance test" as used here represents the "paper and paperboard stiffness testing method using a pressing bend method (Gurley method)," described in "pulp and paper testing methods", J.TAPPI (JAPAN TAPII) No. 40-83, issued by Japan Technical Association of the Pulp and Paper Industry. Specifically, the absorber is preferably formed with a stiffness of 50 mN to 300 mN at the portion around the first folding portion, and with a stiffness of 15 mN to 45 mN at the first folding portion. Furthermore, the absorber is more preferably formed with a stiffness of 150 mN to 250 mN at the portion around the first folding portion, and with stiffness of 25 mN to 35 mN at the first folding portion.

In a sixth aspect of the nursing pad as described in the first through fifth aspect of the present invention, the first folding portion has a thickness of the absorber which is different from the thickness of absorber around the first folding portion.

With the nursing pad described in sixth aspect of the present invention, there is a difference in the thickness of the absorber between the first folding portion and the portion around the first folding portion. Specifically, the absorber may be formed with a lower thickness at the first folding portion than the portion around the first folding portion. Conversely, the absorber may be formed with a higher thickness at the first folding portion than the portion around the first folding portion. In either arrangement, the nursing pad main body is folded along the boundary across which the thickness changes. Accordingly, such an arrangement allows the wearer to easily wear it again while effectively preventing the nursing pad main body from losing its shape.

In a seventh aspect of the nursing pad as described in the first through sixth aspect of the present invention, the first folding portion has a basic weight of the absorber which is different from the basic weight of absorber around the first folding portion.

With the nursing pad described in seventh aspect of the present invention, there is a difference in the basic weight of the absorber between the first folding portion and the portion around the first folding portion. Specifically, the absorber may be formed with a lower basic weight at the first folding portion than the portion around the first folding portion. Conversely, the absorber may be formed with a higher basic weight at the first folding portion than the portion around the first folding portion. In either arrangement, the nursing pad main body is folded along the boundary across which the basic weight changes. Accordingly, such an arrangement allows the wearer to easily wear it again while effectively preventing the nursing pad main body from losing its shape. Specifically, the absorber is preferably formed with a basic weight which is equal to or greater than $100\ g/m^2$ and is equal to or smaller than $500\ g/m^2$ at the portion around the first folding portion, and with a basic weight which is greater than $0\ g/m^2$ and is equal to or smaller than $100\ g/m^2$ at the first folding portion.

In an eighth aspect of the nursing pad as described in the first through seventh aspect of the present invention, the first folding portion is formed by pressing.

The nursing pad described in the eighth aspect of the present invention has the first folding portion formed by pressing. Specific examples of pressing methods include the embossing method, etc. The first folding portion thus formed by pressing provides the difference in the stiffness between the first folding portion and the portion around the first folding portion. Accordingly, the nursing pad main body can be easily folded along the boundary. This allows the wearer to easily wear it again while effectively preventing the nursing pad main body from losing its shape.

In a ninth aspect of the nursing pad as described in the first through fifth aspect of the present invention, the first folding portion is formed without involving the absorber.

The nursing pad described in the ninth aspect of the present invention has the first folding portion without involving the aforementioned absorber. The liquid-permeable sheet and the liquid-impermeable sheet are preferably directly adhered to each other at the first folding portion formed without involving the absorber. This provides the difference in the stiffness between the first folding portion and the portion around the first folding portion. Accordingly, the nursing pad main body can be easily folded along the boundary. This allows the wearer to easily wear it again while effectively preventing the nursing pad main body from losing its shape.

In a tenth aspect of the nursing pad as described in the first through ninth aspect of the present invention, the liquid-impermeable sheet includes bending responsive means.

With the nursing pad described in the tenth aspect of the present invention, the liquid-impermeable sheet includes a bending responsive means. With such an arrangement, the bending responsive means provides the resistance force which prevents the nursing pad from losing its shape. Here the term "bending responsive means" refers to a means for resisting the bending force against the nursing pad. The bending responsive means acts on the nursing pad of the present invention to restore its shape. Furthermore, the resistance force also serves as the restoring force which allows the nursing pad to be easily restored to the normal state as before. This allows the wearer to easily wear the nursing pad again after breastfeeding. Specific examples of the bending responsive means include an arrangement in which an elastic member is provided to the liquid-impermeable sheet, etc.

In an eleventh aspect of the nursing pad as described in the tenth aspect of the present invention, the bending-responsive means is provided across the first folding portion.

With the nursing pad described in the eleventh aspect of the present invention, the bending-responsive means is provided across the first folding portion. With such an arrangement, the resistance force is applied in the direction along the bending-responsive means formed across the first folding portion that serves as a folding axis which allows the nursing pad main body to be folded therealong. Accordingly, such an arrangement provides superior restoring force, thereby restoring the folded nursing pad main body to the normal state as before. This allows the wearer to easily wear it again, while effectively preventing the nursing pad main body from losing its shape.

In a twelfth aspect of the nursing pad as described in any one of the first through eleventh aspect of the present invention, the nursing pad main body has a second folding portion, which serves as a folding axis that allows the nursing pad main body to be folded therealong, formed such that it passes through near the apex of the nursing pad, and extends up to around the perimeter of the nursing pad, and wherein the second folding portion is provided approximately orthogonal to the first folding portion.

The nursing pad described in the twelfth aspect of the present invention includes the second folding portion provided orthogonal to the first folding portion, in addition to the first folding portion. With such an arrangement, the nursing pad main body can be easily folded along the second folding portion, as well as along the first folding portion. Such an arrangement more effectively prevents the nursing pad from losing its shape, thereby allowing the wearer to more easily wear it again.

Advantages

The present invention provides a disposable nursing pad which allows the wearer to easily wear it again while preventing the nursing pad from losing its shape during the breastfeeding.

DETAILED DESCRIPTION OF THE INVENTION

Description will be made regarding embodiments according to the present invention with reference to the drawings. Note that, in embodiments other than a first embodiment, description will be omitted regarding the same components and the same operations and effects as those in the first embodiment.

First Embodiment

Overall Structure of a Nursing Pad

Figure 1:
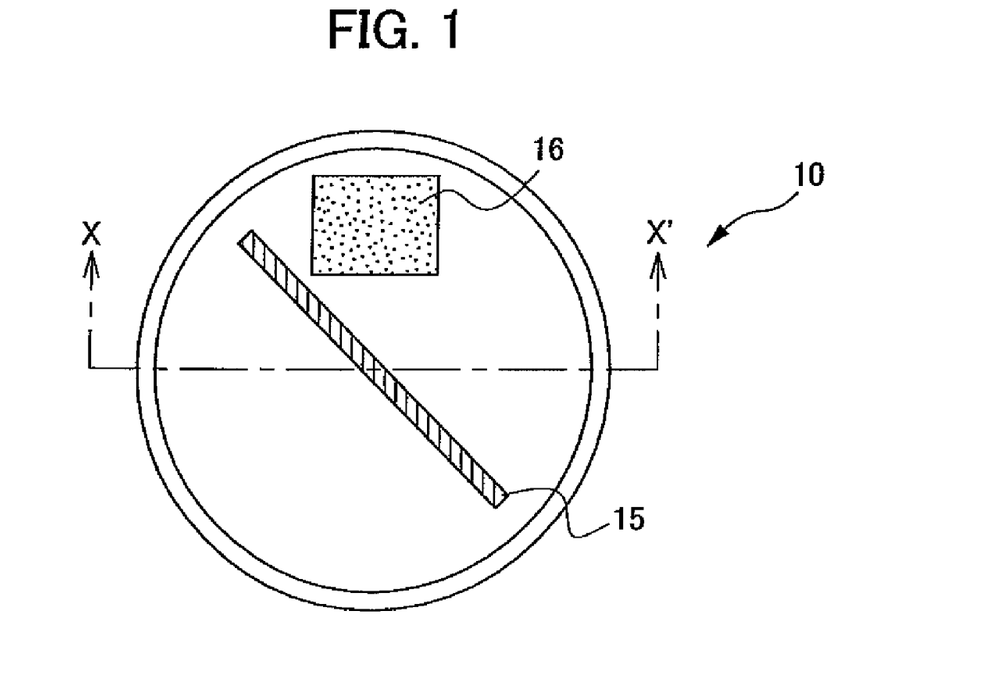
FIG. 1 is a plan view of a nursing pad main body according to a first embodiment as viewed from the outside (from the side of the clothing)
Figure 2:
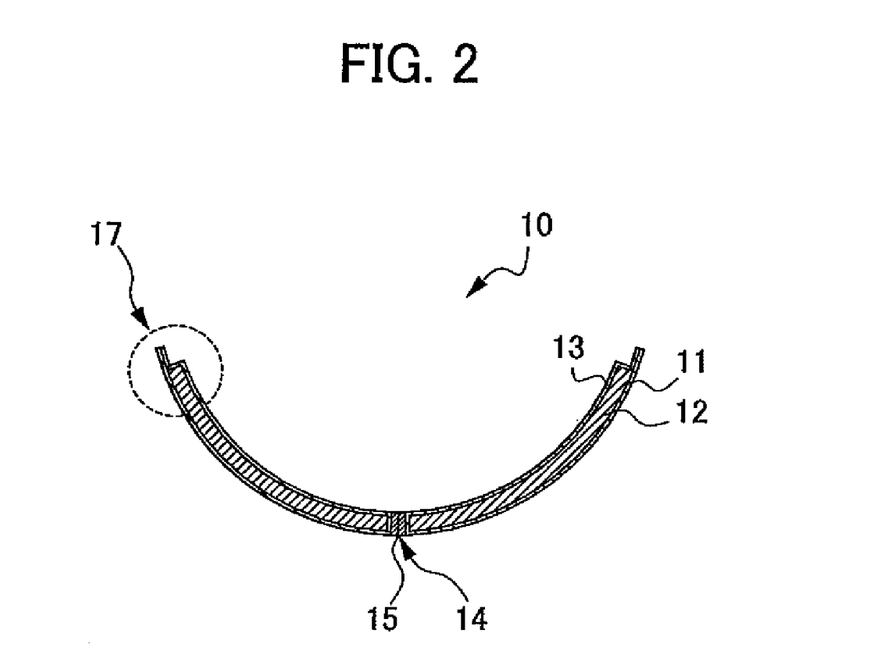
FIG. 2 is a cross-sectional view taken along line X-X' in FIG. 1.
Figure 3:
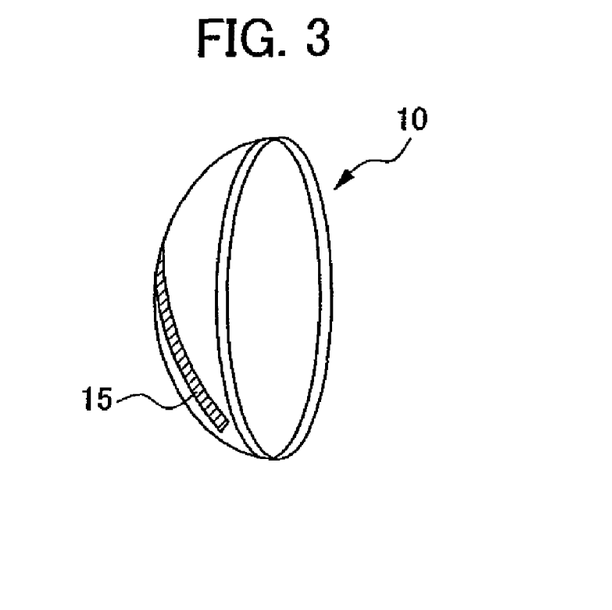
FIG. 3 is a perspective view of the nursing pad main body according to the first embodiment.

A nursing pad according to a first embodiment is formed of a pair of nursing pad main bodies. Note that description will be made in the present embodiment regarding only a nursing pad main body 10 for the wearer's right breast for the sake of simplification. FIG. 1 is a plan view of the nursing pad main body 10 as viewed from the outside (from the side of the clothing). FIG. 2 is a cross-sectional view taken along line X-X' in FIG. 1. FIG. 3 is a perspective view of the nursing pad main body 10. FIG. 4 is a diagram which shows the wearer wearing the nursing pad main body 10. As shown in these drawings, the nursing pad main body 10 is formed in the shape of a dome, which allows the nursing pad main body 10 to envelop the wearer's breast. Note that the nursing pad main body 10 is also preferably formed in an approximately conical shape, as well as the shape of a dome. Also, the shape of the nursing pad main body 10 is not restricted in particular, as long as the nursing pad is formed in a shape that fits the wearer's breast.

Nursing Pad

The nursing pad main body 10 includes: a liquid-impermeable sheet 11 which forms the external shape; a liquid-permeable sheet 13 having liquid permeability provided on the inner face of the liquid-impermeable sheet 11 with the perimeter thereof being adhered to the perimeter of the liquid-impermeable sheet 11; and an absorber 12, which is provided between the liquid-impermeable sheet 11 and the liquid-permeable sheet 12, and has a function of absorbing and holding the mother's milk.

The aforementioned nursing pad main body 10 has a first folding portion 15, which serves as a folding axis along which the nursing pad main body 10 can be folded. The first folding portion is formed such that it passes through near the apex 14 of the nursing pad main body 10, and extends around the perimeter portion 17. With such an arrangement, the aforementioned first folding axis is formed such that it extends obliquely from the lower-inner side to the upper-outer side of the wearer's breast when the nursing pad main body 10 is being worn. Furthermore, a fastening means 16 is provided to a part of the liquid-impermeable sheet 11, except for the first folding portion 15, and for the linear portion orthogonal to the first folding portion 15. The fastening means 16 allows the nursing pad main body 10 to be fastened to the wearer's clothing.

Liquid-permeable Sheet

The liquid-permeable sheet 13 is provided on the inner face of the dome-shaped nursing pad main body 10. Accordingly, the liquid-permeable sheet 13 is directly in contact with the wearer's breast, and is formed of a material which feels soft. Furthermore, the liquid-permeable sheet 13 needs to receive the mother's milk, and to introduce the mother's milk to the absorber 12 provided on the outside thereof. Accordingly, the liquid-permeable sheet 13 is formed of a liquid-permeable material. Specifically, the liquid-permeable sheet 13 is formed of hydrophilic fibrous non-woven fabric. Alternatively, the liquid-permeable sheet 13 is formed of hydrophobic fibrous non-woven fabric or film having a great number of pores.

Liquid-impermeable Sheet

The liquid-impermeable sheet 11 is provided on the outer face of the dome-shaped nursing pad main body 10, and forms the external shape of the nursing pad main body 10. The liquid-impermeable sheet 11 is formed of a liquid-impermeable material such that it protects the wearer's clothing from being damp due to an undesired leakage of the mother's milk held by the absorber 12. Specific examples of such materials include: a moisture-permeable and liquid-impermeable drawn plastic film containing inorganic fine particles such as silica, alumina, or the like; a laminate of a liquid-impermeable film and a fibrous non-woven fabric; a laminate of a moisture-permeable and liquid-impermeable film and a fibrous non-woven fabric, etc. Also, liquid-impermeable sheet 11 may be formed of a composite non-woven fabric having a laminate structure of spunbonded non-woven fabric and a meltblown non-woven fabric.

Absorber

The absorber 12 is formed of a mixture of particulate or fibrous high water absorption polymer and fluff pulp, or a mixture of particulate or a fibrous high water absorption polymer, fluff pulp, and thermoplastic synthetic resin fiber. More specifically, such a mixture is pressed into a sheet with a predetermined thickness, thereby forming the absorber 12. The absorber 12 is formed with a predetermined thickness over the entire area by press processing. Thus, the absorber 12 exhibits a higher stiffness than that of the liquid-permeable sheet 13 and the liquid-impermeable sheet 11 described above. Note that the entire area of the absorber 12 is preferably wrapped in tissue paper in order to prevent the absorber 12 from losing its shape, and to prevent the polymer from escaping from the absorber.

The absorber 12 is adhered to the inner face of the liquid-permeable sheet 13 or the liquid-impermeable sheet 11 through the tissue paper using a hot melt adhesive or the like. Note that an arrangement may be made employing an SM non-woven fabric or an SMS non-woven fabric, instead of the tissue paper. Here, the SM non-woven fabric and the SMS non-woven fabric are each a composite non-woven fabric formed in the shape of a sheet having a laminate structure in which a fibrous non-woven fabric, which is formed with a high strength and high flexibility using a spun-bonding method, is provided to at least one face of a fibrous non-woven fabric which is formed with a high fiber density using a meltblown method. In other words, the SM non-woven fabric and the SMS non-woven fabric have a multi-layered structure of spunbonded non-woven fabrics and meltblown non-woven fabrics. With such an arrangement, employing such a composite non-woven fabric, the fibers which form the fabric exhibit hydrophobicity. Accordingly, the absorber is preferably subjected to hydrophilic processing in order to improve the liquid-permeability. Note that examples of high water absorption polymers employed include: a starch polymer, a cellulose polymer, a synthetic polymer, etc.

The adhesive is applied to the liquid-impermeable sheet 11, the liquid-permeable sheet 13, and the absorber 12, in any one of: a spiral manner, an undulating manner, a zigzag manner, a dotted manner, and a stripe manner. With the present embodiment, the adhesive is applied to such a component sheet in such an application manner. Accordingly, the liquid-impermeable sheet 11 and the liquid-permeable sheet 13 are adhered to each other in a discontinuous manner, thereby adhering the absorber 12 to the liquid-impermeable sheet 11 and the liquid-permeable sheet 13 in a discontinuous manner. As an adhesive, a hot melt adhesive or the like is employed. Either an olefin adhesive or a styrene rubber adhesive can be employed as such an adhesive.

The fibrous non-woven fabric which can be employed in the present embodiment may be manufactured using any one of: a spun-lace method, a needle punch method, a meltblown method, a thermal-bond method, a spun-bonding method, and a chemical-bonding method. The hydrophilic fibrous non-woven fabric can be formed of any one fiber selected from among: a synthetic fiber, semi-synthetic fiber, and a regenerated fiber, which have been subjected to hydrophilic processing, or a composite fiber formed of a mixture of these fibers. The hydrophobic fibrous non-woven fabric can be formed of synthetic fiber. The hydrophobic fibrous non-woven fabric may contain a semi-synthetic fiber and regenerated fiber, which have been subjected to water-repellent processing. The synthetic fiber which can be employed is not restricted in particular. Specific examples of the synthetic fibers which can be employed include: a polyester fiber, a polyacrylonitrile fiber, a polyvinyl chloride fiber, a polyethylene fiber, a polypropylene fiber, and a polystyrene fiber. Examples of the synthetic fibers which can be employed include: a sheath-core type composite fiber, a parallel-type composite fiber, a non-circular hollow fiber, microporous fiber, junction composite fiber, etc.

First Folding Portion

The first folding portion 15 is formed such that it passes through near the apex 14 of the nursing pad main body 10, and extends around the perimeter portion 17. With such an arrangement, the aforementioned first folding portion 15 is formed such that it extends obliquely with respect to the vertical axis of the wearer's body from the lower-inner side of the wearer's breast, D and I, to the upper-outer side thereof, U and O, when the nursing pad main body 10 is being worn. With such an arrangement, the absorber 12 is formed with different properties such as thickness, basic weight, or the like, at the first folding portion 15 as compared with the portion around the first folding portion, thereby providing the difference in the stiffness between the first folding portion 15 and the portion therearound.

Also, an arrangement may be made in which the absorber is not provided to the first folding portion formed such that it passes through the near the apex of the nursing pad main body, and extends up to around the perimeter; and the liquid-permeable sheet and the liquid-impermeable sheet are directly adhered to each other using a hot melt adhesive, thereby forming the first folding portion. Such an arrangement also provides the difference in the stiffness between the first folding portion and the portion around the first folding portion. Specifically, the liquid-impermeable sheet and the liquid-permeable sheet are divided respectively into two which are liquid-impermeable sheet pieces and liquid permeable sheet pieces, and a separate absorber piece is sandwiched between a separate liquid-impermeable sheet piece and a separate liquid-permeable sheet piece, thereby forming a nursing pad piece. The same can be said of the other nursing pad piece. The pad piece and the other pad piece thus obtained are adhered to each other using a hot melt adhesive, thereby forming the nursing pad having the first folding portion.

A preferable modification may be made in which the liquid-impermeable sheet has a bending-responsive means positioned across the first folding portion. Examples of such a bending-responsive means include an elastic member and so forth, provided across the first folding portion. A panel formed in the shape of a sheet having elasticity is employed as such an elastic member. For example, a sheet formed of a foam material, and a non-woven fabric such as a spunbonded non-woven fabric, through-air non-woven fabric, SMS non-woven fabric, etc., formed with a basic weight of 30 g/m$^2$ or more, exhibits increased elasticity. Accordingly, such sheets are employed as the elastic member having a function of satisfactorily resisting, and restoring a shape.

Fastening Means

The liquid-impermeable sheet 11, which is a component of the nursing pad main body 10, has a fastening means 16 provided to a portion other than the first folding portion 15 and the linear portion orthogonal to the first folding portion 15, which allows the nursing pad main body 10 and the wearer's clothing to be fastened to each other. Let us consider an arrangement in which the fastening means 16 is provided on the first folding portion 15. In some cases, such an arrangement has a problem of preventing the nursing pad main body 10 from being folded along the first folding portion 15 which serves as a folding axis. On the other hand, in general, the wearer wears the nursing pad with the fastening means being positioned on the upper side. Accordingly, with such an arrangement in which the fastening means 16 is provided on the first folding portion 15, the first folding portion 15 does not extend obliquely on the wearer's breast when the nursing pad is being worn by the wearer. Accordingly, such an arrangement does not provide the advantage of the present invention. The same can be said of another arrangement in which the fastening means 16 is provided on the linear portion orthogonal to the first folding portion 15. Note that it is sufficient for the present embodiment that the center of the fastening means 16 is provided at a portion other than the first folding portion 15 and the linear portion orthogonal to the first folding portion 15. In other words, an arrangement may be made in which the edge of the fastening means 16 overlaps with the first folding portion 15 or the linear portion orthogonal to the first folding portion 15. Specific examples of the fastening means 16 include: means in which a styrene rubber adhesive is applied; means in which a male mechanical fastener having multiple hooks is provided. Note that multiple sets in which such a fastening means 16 may be provided. The multiple sets of a fastening means 16 may be provided, in particular, in a symmetrical manner with respect to the first folding portion 15. Such an arrangement allows the nursing pad to be used for both the left and the right breast.

Operation and Effects

A description will be made regarding the operation and effects of the nursing pad according to the present embodiment. The wearer generally wears a nursing pad with the fastening means being positioned on the upper side, the reason being that such an arrangement allows the wearer to easily wear the nursing pad, and allows the wearer to expose/unexposed the wearer's breast when the wearer breast-feeds a baby. With the present embodiment, the nursing pad main body 10 has the first folding portion 15, which serves as a folding axis of the nursing pad main body 10, formed such that is passes through near the top of the nursing pad, and extends up to around the perimeter of the nursing pad. Furthermore, the fastening means 16, which allows the nursing pad main body 10 to be fastened to the wearer's clothing, is provided to a portion on the side having the liquid-impermeable sheet other than the first folding portion 15 and the linear portion orthogonal to the first folding portion 15. This ensures that the first folding portion is positioned obliquely on the wearer's breast when the wearer is wearing the nursing pad with the fastening means 16 being positioned on the upper side, as is habitually performed. Also, the wearer knows the shape of a bra used in daily life. Accordingly, it is natural for the wearer to wear the nursing pad with the first folding portion 15 being positioned such that it extends obliquely from the upper-outer side to the lower-inner side of the wearer's breast. With such an arrangement in which the nursing pad is being worn with the first folding portion 15 being positioned such that it extends obliquely from the upper-outer side to the lower-inner side of the wearer's breast, let us consider a case in which the wearer displaces the bra downward and obliquely when the wearer breast-feeds a baby. In this case, the nursing pad main body 10 is folded in a form following the shape of the wearer's breast with the first folding portion 15 as a folding axis. That is to say, the nursing pad main body 10 is folded along the first folding portion 15, thereby effectively preventing the nursing pad main body 10 from losing its shape. This allows the wearer to easily wear the nursing pad again together with the bra in the normal state as before. Furthermore, such an arrangement prevents mother's milk stored in the absorber 12 from leaking due to the absorber 12 being twisted. Furthermore, the nursing pad main body 10 moves on with the bra through the fastening means 16. This effectively prevents the nursing pad main body 10 from losing its shape, thereby allowing the wearer to wear the nursing pad main body 10 again together with the bra in the normal state as before.

Second Embodiment

Figure 5:
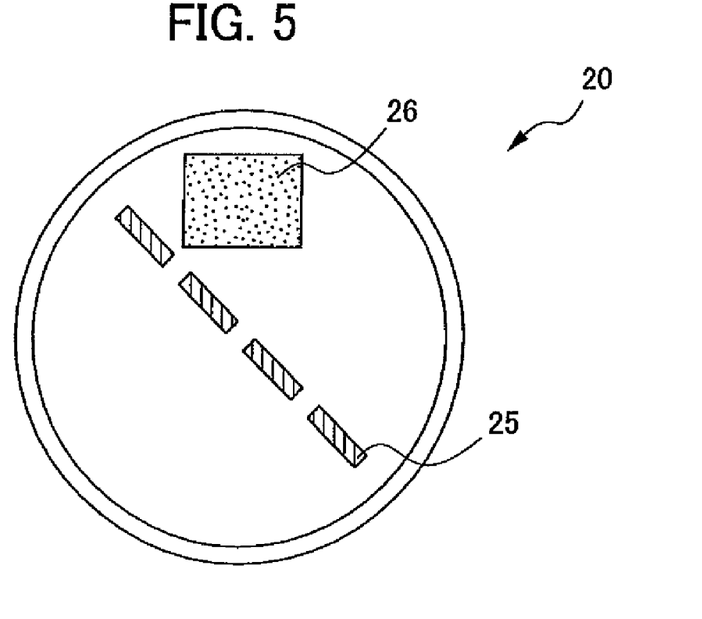
FIG. 5 is a plan view of a nursing pad main body according to a second embodiment as viewed from the outside (from the side of the clothing)

FIG. 5 is a plan view which shows a nursing pad main body 20 according to a second embodiment as viewed from the external side (from the side of the wearer's clothing). As shown in FIG. 5, the nursing pad main body 20 has the first folding portion 15 formed in a discontinuous manner, unlike the nursing pad main body 10 according to the first embodiment having the first folding portion 15 formed in a continuous manner. Specifically, with the present embodiment, multiple first folding portions 25 are provided at a predetermined interval. The interval is determined as appropriate giving consideration to the balance between the flexibility of the nursing pad main body 20 and the water absorption capacity thereof. With the nursing pad main body 20 according to the present second embodiment, the absorber 22 is not divided by the first folding portion 25. With such an arrangement, the mother's milk is absorbed by the entire area of the absorber 22, thereby providing superior water absorption capacity.

Third Embodiment

Figure 6:
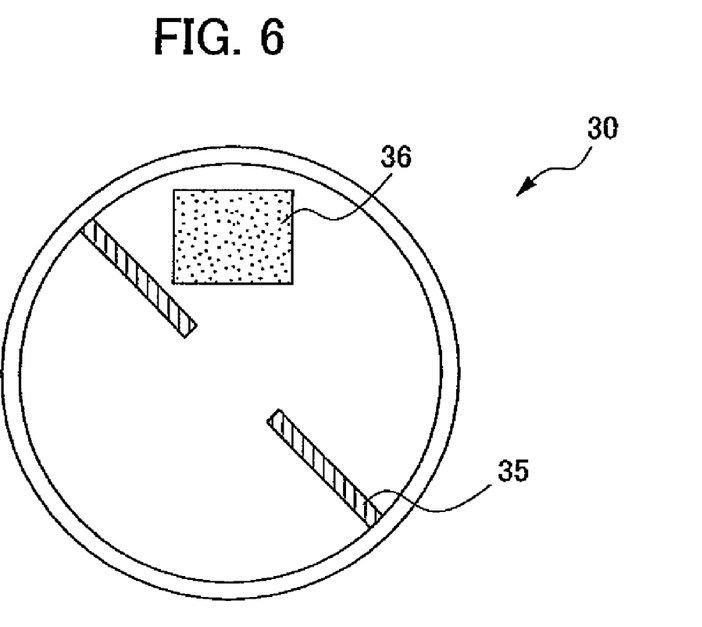
FIG. 6 is a plan view of a nursing pad main body according to a third embodiment as viewed from the outside (from the side of the clothing)

FIG. 6 is a plan view which shows a nursing pad main body 30 according to a third embodiment as viewed from the external side (from the side of the wearer's clothing). As shown in FIG. 6, the nursing pad main body 30 has the first folding portion 15 formed in a discontinuous manner, unlike the nursing pad main body 10 according to the first embodiment having the first folding portion 15 formed in a continuous manner. Furthermore, with the third embodiment, the first folding portion 15 is provided to portions other than the portion with which the wearer's nipple is in contact with when the nursing pad main body 30 is being worn. Specifically, first folding portions 35 according to the present embodiment are each provided to parts of a linear portion which passes through near the apex 14 of the dome-shaped nursing pad main body 30, and which extends up to around the perimeter of the nursing pad main body 50, except for the portion with which the wearer's nipple is to be in contact with. In other words, the first folding portion 35 is provided to each of both end portions of the aforementioned linear portion other than the center portion (the upper and lower portions in the drawing) in a continuous manner. Also, the first folding portion 35 may be provided to each of the upper and lower portions of the aforementioned linear portion in a discontinuous manner. With the nursing pad main body 30 according to the present third embodiment, the first folding portion 15 is not provided to the portion with which the wearer's nipple is to be in contact with. Such an arrangement suppresses sensations of discomfort when the wearer is wearing the nursing pad main body 30.

Fourth Embodiment

Figure 7:
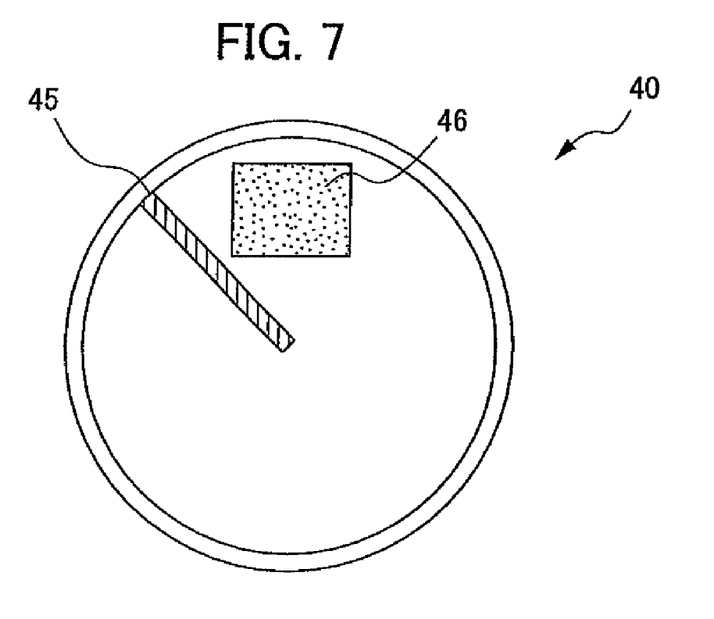
FIG. 7 is a plan view of a nursing pad main body according to a fourth embodiment as viewed from the outside (from the side of the clothing)

FIG. 7 is a plan view which shows a nursing pad main body 40 according to a fourth embodiment as viewed from the external side (from the side of the wearer's clothing). As shown in FIG. 7, the nursing pad main body 40 according to the present embodiment has a first folding portion 35, having only one of either of the aforementioned first folding portions 35, as provided to the nursing pad main body 30 according to the third embodiment. The first folding portion 45 may be formed not only in a continuous manner, but also in a discontinuous manner. With the nursing pad main body 40 according to the fourth embodiment, the first folding portion 35 is provided to minimal area necessary, thereby providing greater comfort and absorption capacity.

Fifth Embodiment

Figure 8:
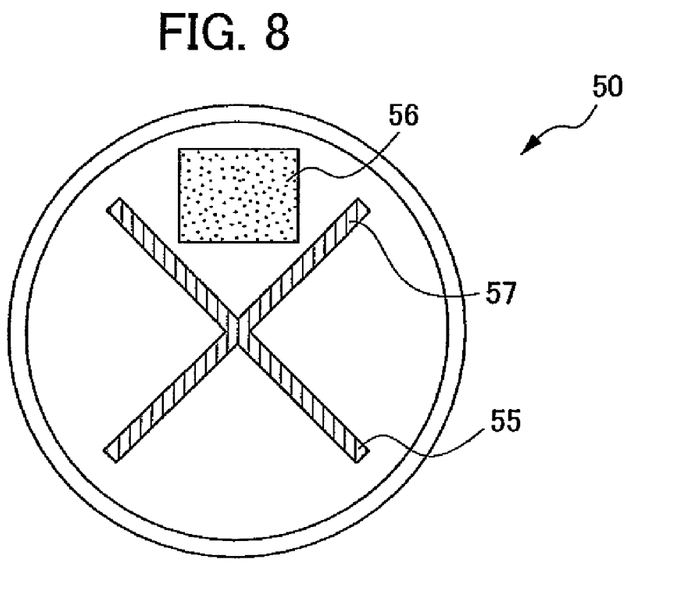
FIG. 8 is a plan view of a nursing pad main body according to a fifth embodiment as viewed from the outside (from the side of the clothing)

FIG. 8 is a plan view which shows a nursing pad main body 50 according to a fifth embodiment as viewed from the external side (from the side of the wearer's clothing). As shown in FIG. 8, the nursing pad main body 50 according to the present embodiment has a second folding portion 57 which serves as a folding axis, and which is formed such that it passes through near the apex 14 of the nursing pad main body 50. The second folding portion 57 is provided such that it passes through the apex 14, and extends around the perimeter of the nursing pad main body 50. Furthermore, the nursing pad main body 50 also has a first folding portion 55 formed approximately orthogonal to the second folding portion 57. The second folding portion 57 is formed in the same way as with the first folding portion 55 as described above. With the present fifth embodiment, such an arrangement allows the nursing pad main body 50 to be easily folded, not only along the first folding portion 55 which serves as a folding axis, but also along the second folding portion 57 which serves as another folding axis. This more effectively prevents the nursing pad main body 50 from losing its shape, thereby allowing the wearer to easily wear it again.

Sixth Embodiment

Figure 9:
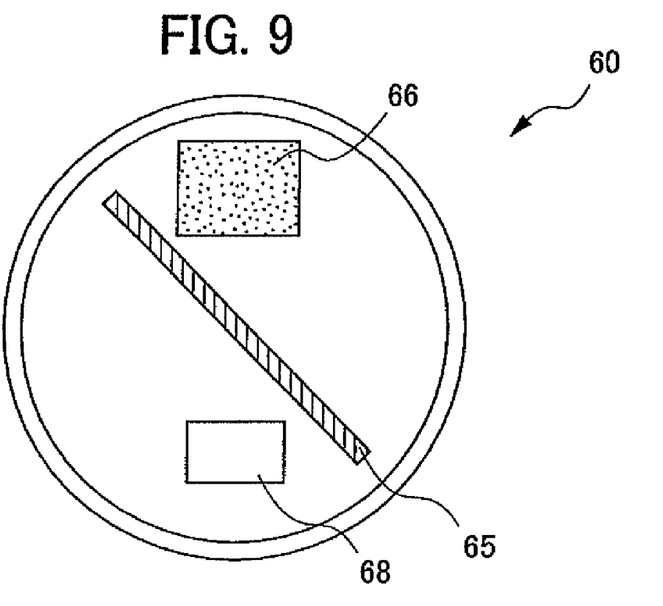
FIG. 9 is a plan view of a nursing pad main body according to a sixth embodiment as viewed from the outside (from the side of the clothing)

FIG. 9 is a plan view which shows a nursing pad main body 60 according to a sixth embodiment as viewed from the external side (from the side of the wearer's clothing). As shown in FIG. 9, the nursing pad main body 60 according to the present embodiment has a display region 68, provided to a liquid-impermeable sheet 61, for displaying a wearing method for the nursing pad 68.

Display Region

Description is being made in the present embodiment regarding an arrangement in which the display region 68 is directly provided to the outer surface (The side of the wearer's skin will be referred to as the "inner side", and the side of the wearer's clothing will be referred to as the "outer side", when the nursing pad is being worn). Note that the portion where the display region is provided is not restricted in particular, as long as the wearer can see the display region from the external side of the nursing pad main body 60. Specifically, the display region 68 may be directly provided to the inner surface of the liquid-permeable sheet 63, as well as an arrangement in which the display region 68 is provided to the outer surface of the liquid-impermeable sheet 61. Also, an arrangement may be made in which the display region 68 is provided to the inner surface or the outer surface of an absorber 62, and the liquid-permeable sheet 63 or the liquid-impermeable sheet has translucency, thereby allowing the wearer to see the display region 68 through the translucent liquid-permeable sheet 63 or the translucent liquid-impermeable sheet 61. Also, the display region 68 may be provided to the edge of the liquid-permeable sheet 63 or the liquid-impermeable sheet 61 in the form of a tag. Also, the display region 68 may be provided such that the fastening means 66 gives the wearer such instructions.

The content of the display region 68 is not restricted in particular, as long as the display region 68 gives the wearer instructions that the nursing pad main body 60 should be worn with a first folding portion 65 being positioned obliquely from the upper-outer side to the lower-inner side of the wearer's breast. For example, the display region 68 may be provided in a form of drawings or texts, which gives the wearer information with respect to the state in which the wearer is to wear the nursing pad main body 60 according to the present embodiment with the first folding portion 65 being positioned obliquely from the upper-outer side to the lower-inner side of the wearer's breast. Alternatively, the display region 68 may be provided in a form which gives the wearer information with respect to the upper side and the lower side of the nursing pad main body 60, thereby guiding the wearer to a proper wearing state.

Operation and Effects

The nursing pad main body 60 according to the present embodiment has the display region 68 which guides the wearer to a proper wearing state in which the nursing pad main body 60 is being worn with the first folding portion 65 being positioned obliquely from the upper-outer side to the lower-inner side of the wearer's breast. Such an arrangement allows the wearer to easily and properly wear the nursing pad main body 60 according to the instructions of the display region 68. Furthermore, the nursing pad main body 60 is easily folded along the first folding portion 65 that serves as a folding axis, in cases that the wearer displaces the nursing pad main body 60 along with the bra downward and obliquely when the wearer breast-feeds a baby. Such an arrangement prevents the nursing pad main body 60 within the bra from folding in an irregular form, thereby effectively preventing the nursing pad main body 60 from losing its shape. Furthermore, in cases that the wearer wears the nursing pad main body 60 again together with the bra after breast-feeding, the nursing pad main body 60 can be easily restored to the normal state, thereby allowing the wearer to easily wear it again.

While preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention.

What is claimed is:

1. A nursing pad formed, in a pre-use state, in a substantially dome shape that allows a wearer's breast to be enveloped, wherein the nursing pad comprises:
   a liquid-impermeable sheet that forms the external shape of the nursing pad;
   a liquid-permeable sheet which is adhered to the liquid-impermeable sheet along a perimeter of the nursing pad;
   an absorber which is provided between the liquid-impermeable sheet and the liquid-permeable sheet for absorbing and holding the wearer's milk;
   a first folding portion, which serves as a folding axis that allows the nursing pad to be folded therealong; and
   a fastening element for fastening the nursing pad to the wearer's clothing;
   wherein
   the first folding portion passes near an apex of the nursing pad, and extends toward the perimeter of the nursing pad,
   the first folding portion is provided discontinuously on the nursing pad in regions other than the apex with which the wearer's nipple is to be contact, wherein the absorber is present in the first folding portion and a basic weight of the absorber in the first folding portion is different from the basic weight of the absorber at the apex of the pad,
   the fastening element is provided on an upper side of the liquid-impermeable sheet entirely outside of and without intersecting or overlapping both the first folding portion and a linear portion orthogonal to the first folding portion, and
   the first folding portion is confined along one or two straight lines.

2. The nursing pad according to claim 1, further comprising a display region which includes instructions that the nursing pad should be worn with the first folding portion being positioned obliquely from the upper-outer side to the lower-inner side of the wearer's breast.

3. The nursing pad according to claim 1, wherein a stiffness of the absorber in the first folding portion is different from the stiffness of the absorber at the apex of the pad.

4. The nursing pad according to claim 1, wherein a thickness of the absorber in the first folding portion is different from the thickness of the absorber at the apex of the pad.

5. The nursing pad according to claim 1, wherein the first folding portion comprises a compressed portion.

6. The nursing pad according to claim 1, wherein the liquid-impermeable sheet includes a bending-responsive element across the first folding portion.

7. The nursing pad according to claim 6, wherein the bending-responsive element is one selected from the group consisting of a foam material and a non-woven fabric and said bending-responsive element comprises an elastic sheet having a basic weight of at least 30 g/m$^2$.

8. The nursing pad according to claim 6, wherein the bending-responsive element includes an elastic member extending across the first folding portion.

9. The nursing pad according to claim 1, further comprising a second folding portion, which serves as a second folding axis that allows the nursing pad to be folded therealong, passes near the apex of the nursing pad, and extends toward the perimeter of the nursing pad,
wherein the second folding portion is approximately orthogonal to the first folding portion.

10. A nursing pad kit, comprising a pair of nursing pads each as defined in claim 1, wherein
said nursing pad are not identical to each other and differ in a relative position of the respective first folding portion and fastening element,
one of the nursing pads is adapted to be worn on a left breast of the wearer with (i) the respective first folding portion extending obliquely from an upper-outer side to a lower-inner side of the wearer's left breast and (ii) the respective fastening element being positioned on an upper side of the wearer's left breast and to the right of the first folding portion; and
the other of the nursing pads is adapted to be worn on a right breast of the wearer with (i) the respective first folding portion extending obliquely from an upper-outer side to a lower-inner side of the wearer's right breast and (ii) the respective fastening element being positioned on an upper side of the wearer's right breast and to the left of the first folding portion.

11. The nursing pad according to claim 1, wherein said fastening element consists of a single adhesive zone located off-center of the nursing pad.

12. A nursing pad formed in a shape that allows a wearer's breast to be enveloped, wherein the nursing pad comprises:
a liquid-impermeable sheet that forms the external shape of the nursing pad;
a liquid-permeable sheet which is adhered to the liquid-impermeable sheet along a perimeter of the nursing pad;
an absorber which is provided between the liquid-impermeable sheet and the liquid-permeable sheet for absorbing and holding the wearer's milk;
first and second folding portions each of which is confined along a single straight line serves as a folding axis allowing the nursing pad to be folded therealong, passes near but not through an apex of the nursing pad, which the wearer's nipple is to be contact with, and extends toward the perimeter of the nursing pad; and
a fastening element for fastening the nursing pad to the wearer's clothing;
wherein the fastening element is provided on an upper side of the liquid-impermeable sheet outside both the first folding portion and the second folding portion which is orthogonal to the first folding portion.

13. The nursing pad according to claim 12, wherein the fastening element is entirely located outside both the first folding portion and the second folding portion without overlapping or intersecting said first and second folding portions.

14. The nursing pad according to claim 12, wherein the first folding portion has a length which is about the same as a radius of the nursing pad.

15. The nursing pad according to claim 12, wherein said fastening element consists of an adhesive zone located in a quadrant of the nursing pad, said quadrant being bordered by the first and second folding portions and the perimeter of the nursing pad.

16. The nursing pad according to claim 12, wherein
the nursing pad is formed, in a pre-use state, in a substantially dome shape that allows the wearer's breast to be enveloped; and
the absorber is present in the folding portions and a basic weight of the absorber in the folding portions is different from the basic weight of the absorber at the apex of the pad.

17. A nursing pad formed in a shape that allows a wearer's breast to be enveloped, wherein the nursing pad comprises:
a liquid-impermeable sheet that forms the external shape of the nursing pad;
a liquid-permeable sheet which is adhered to the liquid-impermeable sheet along a perimeter of the nursing pad;
an absorber which is provided between the liquid-impermeable sheet and the liquid-permeable sheet for absorbing and holding the wearer's milk;
a plurality of first zones arranged intermittently along a folding axis for allowing the nursing pad to be folded therealong;
a second zone as a remainder of the pad that does not overlap the first zones;
a fastening element for fastening the nursing pad to the wearer's clothing, said fastening element being provided in the second zone on an upper side of the liquid-impermeable sheet outside the folding axis along which the first zones are arranged,
wherein the first zones are spaced along the folding axis from each other by said second zone and are absent from a central region of the second zone, which the wearer's nipple is to be contact with,
wherein the absorber is present in the first zone and at least one of (a) a stiffness, (b) a thickness, (c) a basic weight of the absorber in the first zone is different from that of the absorbent in the second zone.

18. The nursing pad according to claim 17, wherein said first zones consists of two segments each extending from the perimeter of the pad toward the other and being spaced along the folding axis from the other by the central region of the second zone.

* * * * *